(12) United States Patent
Tanaka

(10) Patent No.: US 12,285,022 B2
(45) Date of Patent: Apr. 29, 2025

(54) INTERNAL AIR ADJUSTMENT DEVICE

(71) Applicant: DAIKIN INDUSTRIES, LTD., Osaka (JP)

(72) Inventor: Naohiro Tanaka, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 773 days.

(21) Appl. No.: 17/495,912

(22) Filed: Oct. 7, 2021

(65) Prior Publication Data

US 2022/0022476 A1 Jan. 27, 2022

Related U.S. Application Data

(63) Continuation of application No. PCT/JP2020/012603, filed on Mar. 23, 2020.

(30) Foreign Application Priority Data

Apr. 15, 2019 (JP) .................. 2019-076813

(51) Int. Cl.
*B01D 53/00* (2006.01)
*A23B 7/04* (2006.01)
(Continued)

(52) U.S. Cl.
CPC ............... *A23B 7/152* (2013.01); *A23B 7/04* (2013.01); *A61L 9/205* (2013.01); *B01D 53/007* (2013.01);
(Continued)

(58) Field of Classification Search
CPC . A23B 7/152; A23B 7/04; A61L 9/205; A61L 2209/12; B01D 53/007;
(Continued)

(56) References Cited

U.S. PATENT DOCUMENTS

2004/0112211 A1   6/2004  Meirav
2018/0272024 A1*  9/2018  Seo .................... B01D 53/86
(Continued)

FOREIGN PATENT DOCUMENTS

EP     3 318 826 A1    5/2018
JP     H04-75575 A  *  3/1992  ........... A23L 3/3418
(Continued)

OTHER PUBLICATIONS

English translation of the International Preliminary Report on Patentability and Written Opinion of the International Searching Authority for International Application No. PCT/JP2020/012603, dated Oct. 28, 2021.

(Continued)

*Primary Examiner* — Christine T Mui
(74) *Attorney, Agent, or Firm* — Birch, Stewart, Kolasch & Birch, LLP

(57) ABSTRACT

An internal air adjustment device (30) includes an internal-side passage (70) and an internal-side treatment unit (152). The internal-side separator (61) in the internal-side passage (70) separates return air from internal air. The composition of the return air differs from the composition of the internal air. The internal-side passage (70) supplies the return air into a storage (1). The internal-side treatment unit (152) decomposes ethylene in air that flows in the internal-side passage (70). Therefore, the concentration of ethylene of the return air is lower than the concentration of ethylene of the internal air.

3 Claims, 6 Drawing Sheets

(51) Int. Cl.
  *A23B 7/152* (2006.01)
  *A61L 9/20* (2006.01)
  *B01D 53/86* (2006.01)
  *A01F 25/14* (2006.01)
  *B01D 53/34* (2006.01)
  *F25D 17/04* (2006.01)

(52) U.S. Cl.
  CPC ......... *B01D 53/8668* (2013.01); *A01F 25/14* (2013.01); *A23V 2002/00* (2013.01); *A61L 2209/12* (2013.01); *B01D 2255/802* (2013.01); *B01D 2257/7022* (2013.01); *B01D 2257/91* (2013.01); *B01D 2259/804* (2013.01); *F25D 17/042* (2013.01); *F25D 2317/0417* (2013.01)

(58) Field of Classification Search
  CPC .......... B01D 53/8668; B01D 2255/802; B01D 2257/7022; B01D 2257/91; B01D 2259/804; A23V 2002/00
  USPC ...................................... 422/186.3, 186, 129
  See application file for complete search history.

(56) References Cited

U.S. PATENT DOCUMENTS

| | | | |
|---|---|---|---|
| 2019/0141903 A1 | 5/2019 | Takayama et al. | |
| 2020/0253226 A1 | 8/2020 | Kamei et al. | |
| 2020/0254384 A1 | 8/2020 | Kamei et al. | |
| 2020/0282356 A1 | 9/2020 | Kamei et al. | |
| 2021/0161075 A1 | 6/2021 | Takayama et al. | |

FOREIGN PATENT DOCUMENTS

| | | | | | |
|---|---|---|---|---|---|
| JP | 7-313583 A | | 12/1995 | | |
| JP | 9-196546 A | | 7/1997 | | |
| JP | 2002-274608 A | * | 9/2002 | ............... | B65B 1/00 |
| JP | 2017-190935 A | | 10/2017 | | |
| WO | WO 2011/084121 A2 | | 7/2011 | | |
| WO | WO 2012/155907 A1 | | 11/2012 | | |
| WO | WO 2017/003205 A1 | * | 1/2017 | ............. | F25D 17/04 |
| WO | WO 2019/065879 A1 | | 4/2019 | | |
| WO | WO 2019/065884 A1 | | 4/2019 | | |

OTHER PUBLICATIONS

International Search Report, issued in PCT/JP2020/012603, PCT/ISA/210, dated Jun. 16, 2020.

Extended European Search Report for European Application No. 20791088.6, dated Apr. 11, 2022.

* cited by examiner

INTERNAL AIR ADJUSTMENT DEVICE

CROSS REFERENCE TO RELATED APPLICATIONS

This application is a Continuation of PCT International Application No. PCT/JP2020/012603 filed on Mar. 23, 2020, which claims priority under 35 U.S. C. § 119 (a) to Patent Application No. 2019-076813 filed in Japan on Apr. 15, 2019, all of which are hereby expressly incorporated by reference into the present application.

TECHNICAL FIELD

The present disclosure relates to an internal air adjustment device.

BACKGROUND ART

Hitherto, by controlling an internal environment (specifically, for example, the temperature of internal air or the composition of internal air) of a storage, the freshness of perishable products stored in the storage has been preserved. For example, a refrigeration apparatus disclosed in Patent Literature 1 is used for a container that is used for, for example, transportation by sea, and controls the temperature and the composition (specifically, the concentration of oxygen and the concentration of carbon dioxide) of internal air in the container.

CITATION LIST

Patent Literature

PTL 1: Japanese Unexamined Patent Application Publication No. 2017-190935

SUMMARY

A first aspect of the present disclosure is directed to an internal air adjustment device that adjusts a composition of internal air in an inside of a storage (1). The internal air adjustment device includes:
  an internal-side passage (70) including an internal-side separator (61) configured to separate return air whose composition differs from the composition of the internal air in the inside of the storage (1) from the internal air, the internal-side passage (70) sending the internal air to the internal-side separator (61) from the inside of the storage (1) and sending the return air to the inside of the storage (1) from the internal-side separator (61); and
  an internal-side treatment unit (152) configured to perform at least one of trapping and decomposition of ethylene in air that flows in the internal-side passage (70).

DESCRIPTION OF EMBODIMENTS

Embodiments of the present invention are described in detail based on the drawings.

An internal air adjustment device (30) of the present embodiment is provided in a transport container (1) for what is called CA (Controlled Atmosphere) transport. The internal air adjustment device (30) adjusts the composition of air in the transport container (1). In addition, the internal air adjustment device (30) reduces the concentration of bacteria and ethylene of the air in the transport container (1).

Figure 1:
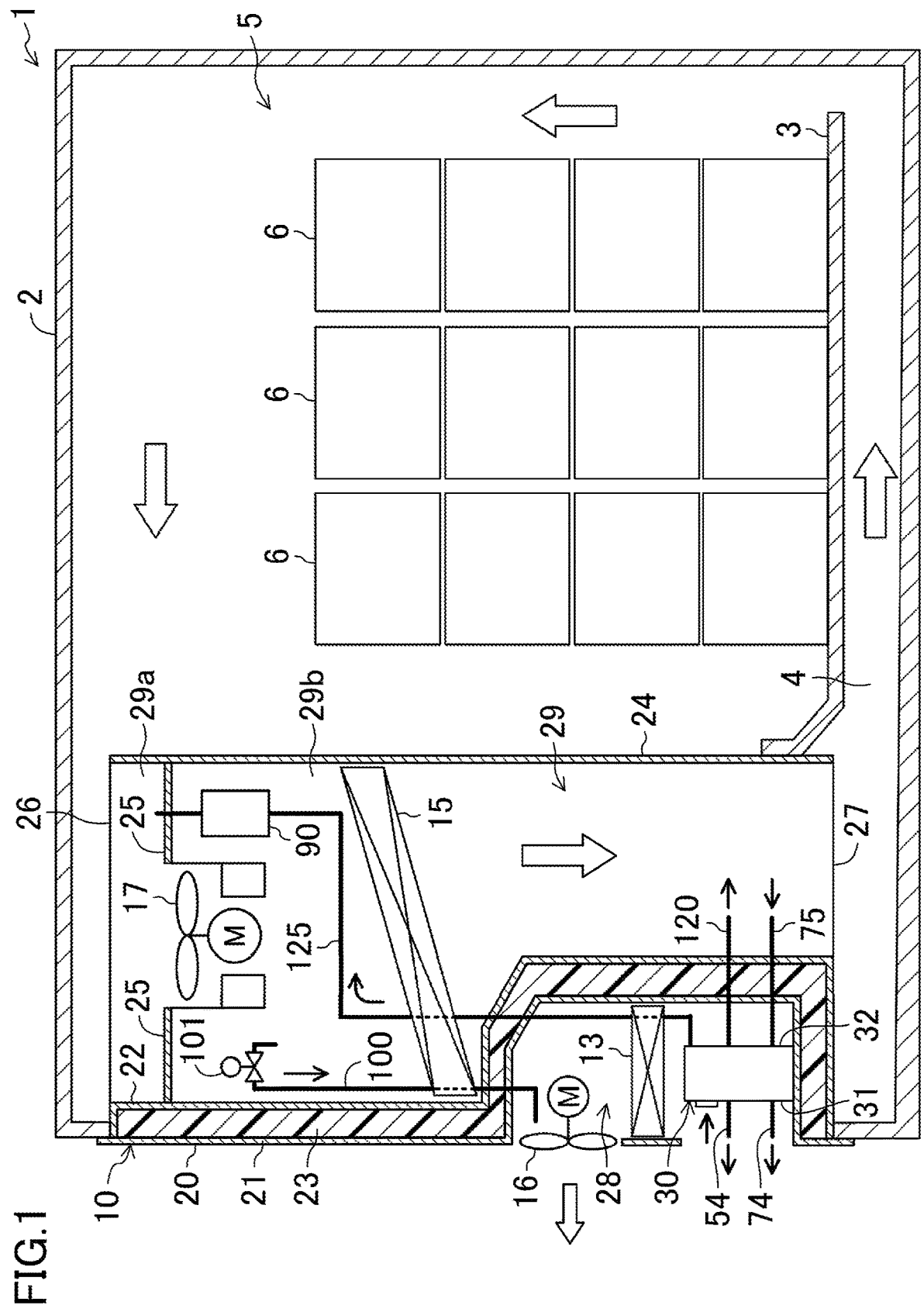
FIG. 1 is a schematic sectional view of a transport container including an internal air adjustment device of an embodiment.

As shown in FIG. 1, the transport container (1) that constitutes a storage includes a container body (2) and a container refrigerating machine (10). The transport container (1) is a reefer container whose internal temperature is controllable. The internal air adjustment device (30) of the present embodiment is installed in the container refrigerating machine (10). The transport container (1) is used for transporting plants that breathe by taking in oxygen ($O_2$) in the air and giving out carbon dioxide ($CO_2$). Examples of plants include, for example, fruits, such as bananas and avocados, vegetables, grains, bulbs, and fresh flowers.

The container body (2) has a box shape that is an elongated rectangular parallelepiped shape. The container body (2) has one end that is open, and has the container refrigerating machine (10) mounted thereon to cover the open end. An internal space of the container body (2) constitutes a load room (5) for storing storage products (6).

A floor plate (3) for placing the storage products (6) thereon is disposed at a bottom portion of the load room (5). An underfloor flow path (4) for allowing air blown out by the container refrigerating machine (10) to flow therein is formed between the floor plate (3) and a bottom plate of the container body (2). The underfloor flow path (4) is a flow path extending in a longitudinal direction of the container body (2) along the bottom plate of the container body (2). One end of the underfloor flow path (4) is connected to a blow-out port (27) of the container refrigerating machine (10), and the other end of the underfloor flow path (4) communicates with a space above the floor plate (3) (that is, a space in which the storage products (6) are to be stored.

—Container Refrigerating Machine—

As shown in FIG. 1, the container refrigerating machine (10) includes a casing (20), a refrigerant circuit (11) that performs a refrigeration cycle, an external fan (16), and an internal fan (17).

The casing (20) includes an external wall portion (21), an internal wall portion (22), a rear plate (24), and a partition plate (25). As described below, the refrigerant circuit (11), the external fan (16), and the internal fan (17) are provided in the casing (20).

The external wall portion (21) is a plate-shaped member that is disposed to cover the open end of the container body (2). A lower portion of the external wall portion (21) bulges toward an inner side of the container body (2). The internal wall portion (22) is a plate-shaped member extending along the external wall portion (21). The internal wall portion (22) is disposed to cover a surface of the external wall portion (21) on the inner side of the container body (2). A space between the external wall portion (21) and the internal wall portion (22) is filled with an insulating material (23).

A lower portion of the casing (20) has a shape that is recessed toward the inner side of the container body (2). The lower portion of the casing (20) forms an external machine room (28) that communicates with a space outside the transport container (1). The external fan (16) is disposed in the external machine room (28).

The rear plate (24) is a flat member having a substantially rectangular shape. The rear plate (24) is disposed more toward the inner side of the container body (2) than the internal wall portion (22) and forms an internal air flow path (29) between the rear plate (24) and the internal wall portion (22). An upper end of the internal air flow path (29) constitutes a suction port (26) of the casing (20), and a lower end of the internal air flow path (29) constitutes the blow-out port (27) of the casing (20).

The partition plate (25) is a plate-shaped member disposed to separate an upper side and a lower side of the internal air flow path (29). The partition plate (25) is disposed at an upper portion of the internal air flow path (29). By the partition plate (25), the internal air flow path (29) is partitioned into a primary flow path (29a) on an upper side of the partition plate (25) and a secondary flow path (29b) on a lower side of the partition plate (25). The primary flow path (29a) communicates with the load room (5) through the suction port (26). The secondary flow path (29b) communicates with the underfloor flow path (4) through the blow-out port (27). The internal fan (17) is mounted on the partition plate 25. The internal fan (17) is disposed to blow out air sucked in from the primary flow path (29a) toward the secondary flow path (29b).

Figure 2:
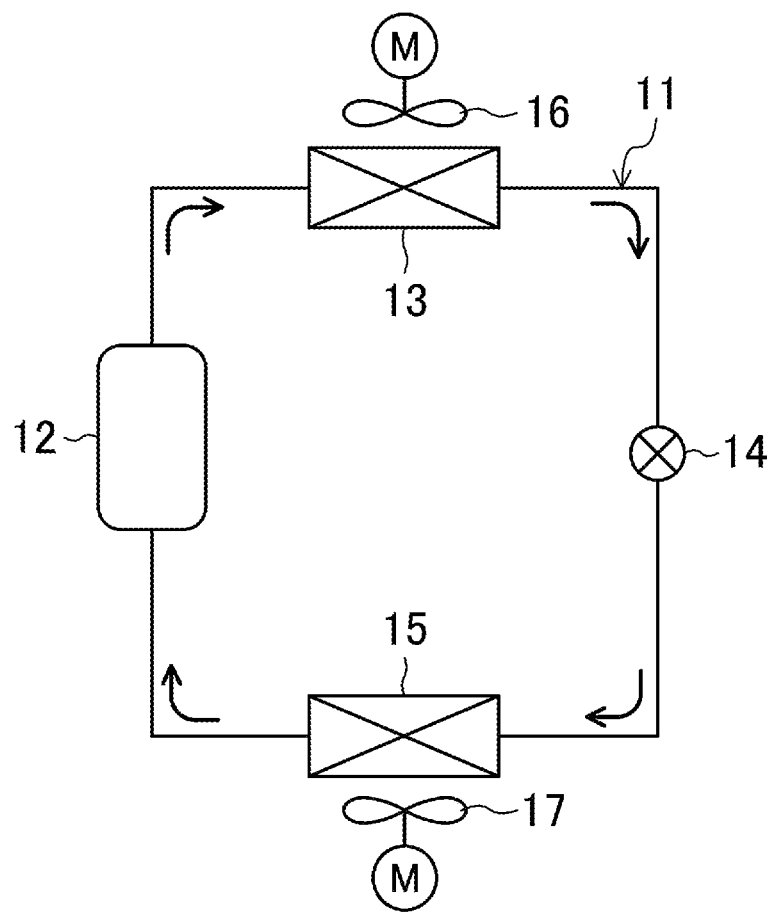
FIG. 2 is a refrigerant circuit diagram showing a a refrigerant circuit of a structure of container refrigerating machine provided in the transport container.

As shown in FIG. 2, the refrigerant circuit (11) is a closed circuit formed by connecting a compressor (12), a condenser (13), an expansion valve (14), and an evaporator (15) by a pipe. When the compressor (12) operates, a refrigerant circulates in the refrigerant circuit (11), and a vapor compression refrigeration cycle is performed. As shown in FIG. 1, the condenser (13) is disposed on a suction side of the external fan (16) in the external machine room (28), and the evaporator (15) is disposed in the secondary flow path (29b) of the internal air flow path (29). Although not shown in FIG. 1, the compressor (12) is disposed in the external machine room (28).

—Internal Air Adjustment Device—

As shown in FIG. 1, the internal air adjustment device (30) includes a body unit (31), a sensor unit (90), a ventilation discharge pipe (100), and a control unit (110). The body unit (31) is installed in the external machine room (28) of the container refrigerating machine (10). The sensor unit (90) is installed in the internal air flow path (29) of the transport container (1). The ventilation discharge pipe (100) is installed to extend from the internal air flow path (29) to the external machine room (28) of the transport container (1). The control unit (110) is provided in the body unit (31), and controls structural components of the internal air adjustment device (30). The sensor unit (90), the ventilation discharge pipe (100), and the control unit (110) are described in detail below.

Figure 3:
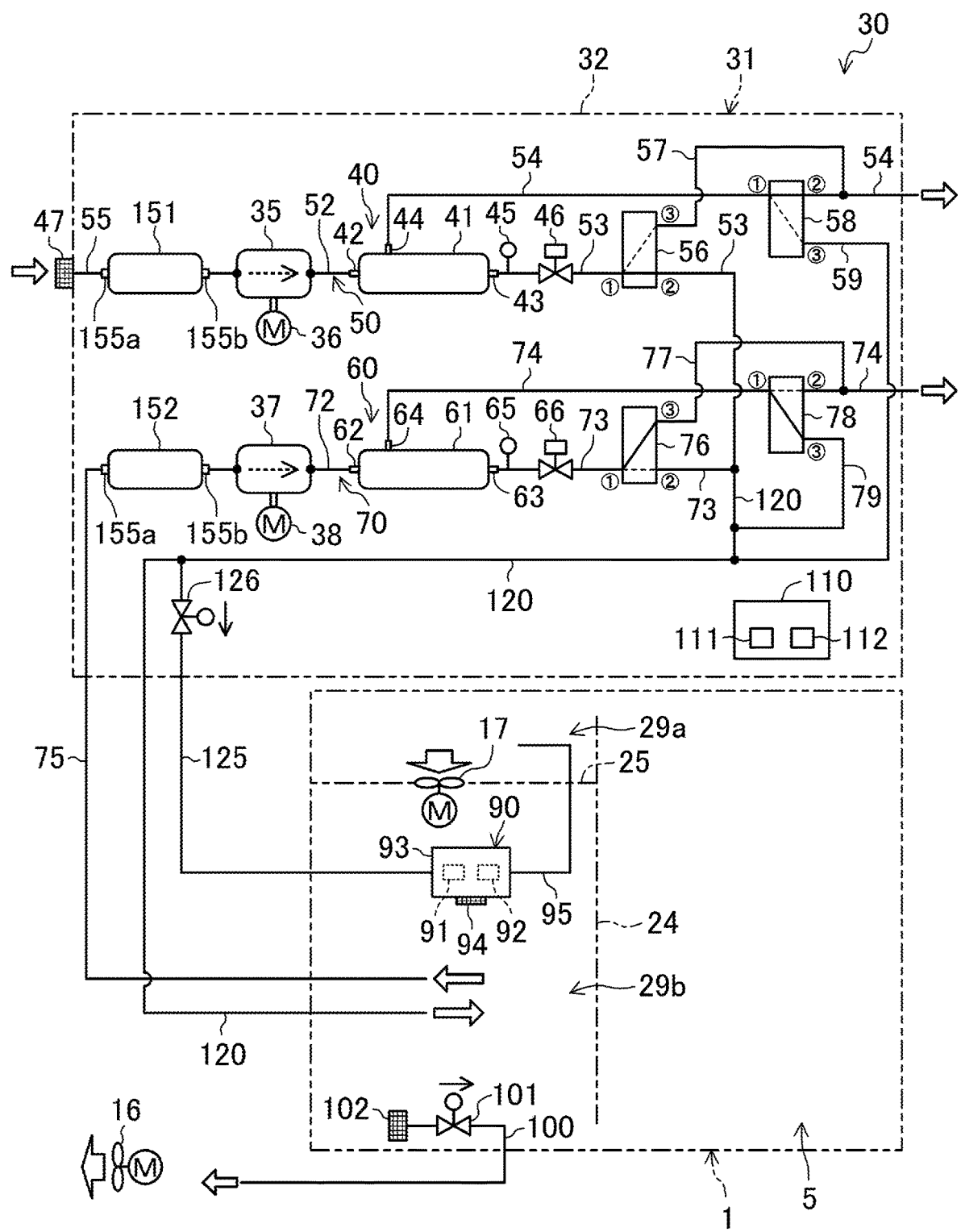
FIG. 3 is a pipe system diagram showing a structure of the internal air adjustment device of the embodiment.

As shown in FIG. 3, the body unit (31) of the internal air adjustment device (30) includes a first composition adjuster (40), a second composition adjuster (60), and a unit case (32). The unit case (32) is a box-shaped hermetically sealed container. The first composition adjuster (40) and the second composition adjuster (60) are disposed in an internal space of the unit case (32). The first composition adjuster (40) and the second composition adjuster (60) are described in detail below.

In addition, the internal air adjustment device (30) includes a supply pipe (120), an internal-side suction pipe (75), and a measurement pipe (125). The supply pipe (120), the internal-side suction pipe (75), and the measurement pipe (125) are pipes for connecting the body unit (31) to the internal air flow path (29) of the container refrigerating machine (10).

The supply pipe (120) is a pipe for supplying into the load room (5) air that has flowed out the first composition adjuster (40) and the second composition adjuster (60). An inlet end of the supply pipe (120) is connected to the first composition adjuster (40) and the second composition adjuster (60), and an outlet end of the supply pipe (120) opens into the secondary flow path (29b) of the internal air flow path (29).

The internal-side suction pipe (75) is a pipe for supplying internal air in the load room (5) to the second composition adjuster (60). An inlet end of the internal-side suction pipe (75) opens into the secondary flow path (29b) of the internal air flow path (29), and an outlet end of the internal-side suction pipe (75) is connected to a second pump (37) of the second composition adjuster (60) described below. Note that, in the secondary flow path (29b) of the internal air flow path (29), the inlet end of the internal-side suction pipe (75) is disposed on an upstream side of the outlet end of the supply pipe (120).

The measurement pipe (125) is a pipe for supplying to the sensor unit (90) air that flows in the supply pipe (120). An inlet end of the measurement pipe (125) is connected to the supply pipe (120), and an outlet end of the measurement pipe (125) is connected to the sensor unit (90). A measurement on-off valve (126) constituted by an electromagnetic valve is provided at the measurement pipe (125). The measurement on-off valve (126) is accommodated in the unit case (32) of the body unit (31).

Note that the ventilation discharge pipe (100), the supply pipe (120), the internal-side suction pipe (75), the measurement pipe (125), and pipes (52 to 55, 71 to 74, 95) that are disposed at the corresponding composition adjuster (40, 60) and that are described below may be constituted by hard pipes, or may be constituted by flexible hoses, or may be constituted by a combination of a pipe and a hose.

<First Composition Adjuster>

The first composition adjuster (40) is constituted to separate external air (untreated external air) that has been sucked in from the outside of the transport container (1) into first external air and second external air. The first composition adjuster (40) supplies one of the first external air and the second external air as supply air to the load room (5) and discharges the other of the first external air and the second external air to the outside of the transport container (1).

The first composition adjuster (40) includes an air filter (47), a first air treatment unit (151), a first pump (35), a first separation module (41), a first pressure sensor (45), a first control valve (46), a first primary switching valve (56), and a first secondary switching valve (58). In addition, the first composition adjuster (40) includes an external-side suction pipe (55), a first introduction pipe (52), a first primary pipe (53), a first secondary pipe (54), a first primary discharge pipe (57), and a first secondary supply pipe (59). Devices and pipes of the first composition adjuster (40) constitute, together with the supply pipe (120), the external-side passage (50). The external-side passage (50) is a passage for supplying to the load room (5) of the transport container (1) air that has passed through the first air treatment unit (151) and the first separation module (41).

The air filter (47) is a membrane filter for trapping, for example, dust or salt in external air. The air filter (47) is mounted on the unit case (32) of the body unit (31). The air filter (47) is connected to the first air treatment unit (151) through the external-side suction pipe (55). Note that, in the internal air adjustment device (30) of the present embodiment, without using the external-side suction pipe (55), the air filter (47) and the first air treatment unit (151) may be connected to each other through the internal space of the unit case (32), which is a hermetically sealed container.

The first air treatment unit (151) constitutes an external-side treatment unit. The first air treatment unit (151) includes a photocatalyst filter (156) and decomposes microbes (such as floating bacteria or mold spores) in untreated external air. The first air treatment unit (151) is described in detail below. The first air treatment unit (151) has an air inlet (155a) and an air outlet (155b). The air inlet (155a) of the first air treatment unit (151) is connected to the air filter (47) through the external-side suction pipe (55). The air outlet (155b) of the first air treatment unit (151) is connected to a suction port of the first pump (35).

The first pump (35) is an air pump that discharges air that has been sucked in. The first pump (35) is constituted by, for example, a displacement-type fluid machine. A first motor (36) is connected to the first pump (35). The first pump (35) is driven by the first motor (36).

The first separation module (41) constitutes an external-side separator. The first separation module (41) includes gas separation membranes (85). The first separation module (41) separates untreated external air into first external air that did not pass through the gas separation membranes (85) and second external air that has passed through the gas separation membranes (85). The first separation module (41) is described in detail below.

The concentration of nitrogen of the first external air is higher than the concentration of nitrogen of the untreated external air, and the concentration of oxygen of the first external air is lower than the concentration of oxygen of the untreated external air. The concentration of nitrogen of the second external air is lower than the concentration of nitrogen of the untreated external air, and the concentration of oxygen of the second external air is higher than the concentration of oxygen of the untreated external air. Note that "concentration" in the present description means volume ratio.

The first separation module (41) has a first introduction port (42), a first primary exit port (43), and a first secondary exit port (44). The first introduction port (42) is connected to a discharge port of the first pump (35) through the first introduction pipe (52). The first primary exit port (43) is connected to the supply pipe (120) through the first primary pipe (53). One end of the first secondary pipe (54) is connected to the first secondary exit port (44). The first secondary pipe (54) extends to the outside of the unit case (32). The other end of the first secondary pipe (54) opens on a suction side of the external fan (16) in the external machine room (28).

The first pressure sensor (45) and the first control valve (46) are provided at the first primary pipe (53). The first pressure sensor (45) is disposed closer than the first control valve (46) to the first separation module (41).

The first pressure sensor (45) measures the pressure of the first external air that has flowed out the first primary exit port (43) of the first separation module (41). The measurement value of the first pressure sensor (45) is substantially equal to the pressure of the untreated external air that is supplied to the first separation module (41) by the first pump (35).

The first control valve (46) is an electrically operated valve whose opening degree is variable. When the opening degree of the first control valve (46) changes, the pressure of the untreated external air that is supplied to the first separation module (41) by the first pump (35) changes.

The first primary switching valve (56) and the first secondary switching valve (58) are each a switching valve having three ports. The first primary switching valve (56) and the first secondary switching valve (58) are each constituted to switch between a first state in which a first port communicates with a second port and is cut off from a third port (state shown by a solid line in FIG. 3) and a second state in which the first port communicates with the third port and is cut off from the second port (state shown by a broken line in FIG. 3).

The first primary switching valve (56) is disposed in the first primary pipe (53). In the first primary pipe (53), the first primary switching valve (56) is disposed closer than the first control valve (46) to the supply pipe (120). The first primary switching valve (56) is such that its first port is connected to the first control valve (46) and its second port is connected to the supply pipe (120). One end of the first primary discharge pipe (57) is connected to the third port of the first primary switching valve (56). The other end of the first primary discharge pipe (57) is connected to the first secondary pipe (54).

The first secondary switching valve (58) is disposed in the first secondary pipe (54). In the first secondary pipe (54), the first secondary switching valve (58) is disposed closer than the other end of the first primary discharge pipe (57) to the first separation module (41). The first secondary switching valve (58) is such that its first port is connected to the first secondary exit port (44) of the first separation module (41) and its second port communicates with the external machine room (28) of the transport container (1) through the first secondary pipe (54). One end of the first secondary supply pipe (59) is connected to the third port of the first secondary switching valve (58). The other end of the first secondary supply pipe (59) is connected to the supply pipe (120).

<Second Composition Adjuster>

The second composition adjuster (60) is constituted to separate internal air (untreated internal air) that has been sucked in from an internal space of the transport container (1) into first internal air and second internal air. The second composition adjuster (60) supplies one of the first internal air and the second internal air as return air to the load room (5), and discharges the other of the first internal air and the second internal air to the outside of the transport container (1).

The second composition adjuster (60) includes a second air treatment unit (152), the second pump (37), a second separation module (internal-side separator) (61), a second pressure sensor (65), a second control valve (66), a second primary switching valve (76), and a second secondary switching valve (78). In addition, the second composition adjuster (60) includes a second introduction pipe (72), a second primary pipe (73), a second secondary pipe (74), a second primary discharge pipe (77), and a second secondary supply pipe (79). Devices and pipes of the second composition adjuster (60) constitute, together with the supply pipe (120), the internal-side passage (70). The internal-side passage (70) is a passage for supplying to the load room (5) of the transport container (1) air that has passed through the second air treatment unit (152) and the second separation module (61).

The second air treatment unit (152) constitutes an internal-side treatment unit. The second air treatment unit (152) includes a photocatalyst filter (156) and decomposes microbes (such as floating bacteria or mold spores) and ethylene in the untreated internal air. The second air treatment unit (152) is described in detail below. The second air treatment unit (152) has an air inlet (155*a*) and an air outlet (155*b*). The air inlet (155*a*) of the second air treatment unit (152) communicates with the inside of the transport container (1) through the internal-side suction pipe (75). The air outlet (155*b*) of the second air treatment unit (152) is connected to a suction port of the second pump (37).

The second pump (37) is an air pump that discharges air that has been sucked in. The second pump (37) is constituted by, for example, a displacement-type fluid machine. A second motor (38) is connected to the second pump (37). The second pump (37) is driven by the second motor (38).

The second separation module (61) constitutes an internal-side separator. The second separation module (61) includes gas separation membranes (85). The second separation module (61) separates untreated internal air into first internal air that did not pass through the gas separation membranes (85) and second internal air that has passed through the gas separation membranes (85). The second separation module (61) is described in detail below.

The concentration of nitrogen of the first internal air is higher than the concentration of nitrogen of the untreated internal air, and the concentration of oxygen and the concentration of carbon dioxide of the first internal air are lower than the concentration of oxygen and the concentration of carbon dioxide of the untreated internal air. The concentration of nitrogen of the second internal air is lower than the concentration of nitrogen of the untreated internal air, and the concentration of oxygen and the concentration of carbon dioxide of the second internal air are higher than the concentration of oxygen and the concentration of carbon dioxide of the untreated internal air.

The second separation module (61) has a second introduction port (62), a second primary exit port (63), and a second secondary exit port (64). The second introduction port (62) is connected to a discharge port of the second pump (37) through the second introduction pipe (72). The second primary exit port (63) is connected to the supply pipe (120) through the second primary pipe (73). One end of the second secondary pipe (74) is connected to the second secondary exit port (64). The second secondary pipe (74) extends to the outside of the unit case (32). The other end of the second secondary pipe (74) opens on the suction side of the external fan (16) in the external machine room (28).

The second pressure sensor (65) and the second control valve (66) are provided at the second primary pipe (73). The second pressure sensor (65) is disposed closer than the second control valve (66) to the second separation module (61).

The second pressure sensor (65) measures the pressure of the second external air that has flowed out the second primary exit port (63) of the second separation module (61). The measurement value of the second pressure sensor (65) is substantially equal to the pressure of the untreated internal air that is supplied to the second separation module (61) by the second pump (37).

The second control valve (66) is an electrically operated valve whose opening degree is variable. When the opening degree of the second control valve (66) changes, the pressure of the untreated internal air that is supplied to the second separation module (61) by the second pump (37) changes.

The second primary switching valve (76) and the second secondary switching valve (78) are each a switching valve having three ports. The second primary switching valve (76) and the second secondary switching valve (78) are each constituted to switch between a first state in which a first port communicates with a second port and is cut off from a third port (state shown by a broken line in FIG. 3) and a second state in which the first port communicates with the third port and is cut off from the second port (state shown by a solid line in FIG. 3).

The second primary switching valve (76) is disposed in the second primary pipe (73). In the second primary pipe (73), the second primary switching valve (76) is disposed closer than the second control valve (66) to the supply pipe (120). The first port of the second primary switching valve (76) is connected to the second control valve (66), and the second port of the second primary switching valve (76) is connected to the supply pipe (120). One end of the second primary discharge pipe (77) is connected to the third port of the second primary switching valve (76). The other end of the second primary discharge pipe (77) is connected to the second secondary pipe (74).

The second secondary switching valve (78) is disposed in the second secondary pipe (74). In the second secondary pipe (74), the second secondary switching valve (78) is disposed closer than the other end of the second primary discharge pipe (77) to the second separation module (61). The second secondary switching valve (78) is such that the first port is connected to the second secondary exit port (64) of the second separation module (61) and the second port communicates with the external machine room (28) of the transport container (1) through the second secondary pipe (74). One end of the second secondary supply pipe (79) is connected to the third port of the second secondary switching valve (78). The other end of the second secondary supply pipe (79) is connected to the supply pipe (120).

<Air Treatment Units>

The structures of the first air treatment unit (151) and the second air treatment unit (152) are described. The structures of the first air treatment unit (151) and the second air treatment unit (152) are the same.

Figure 4A:
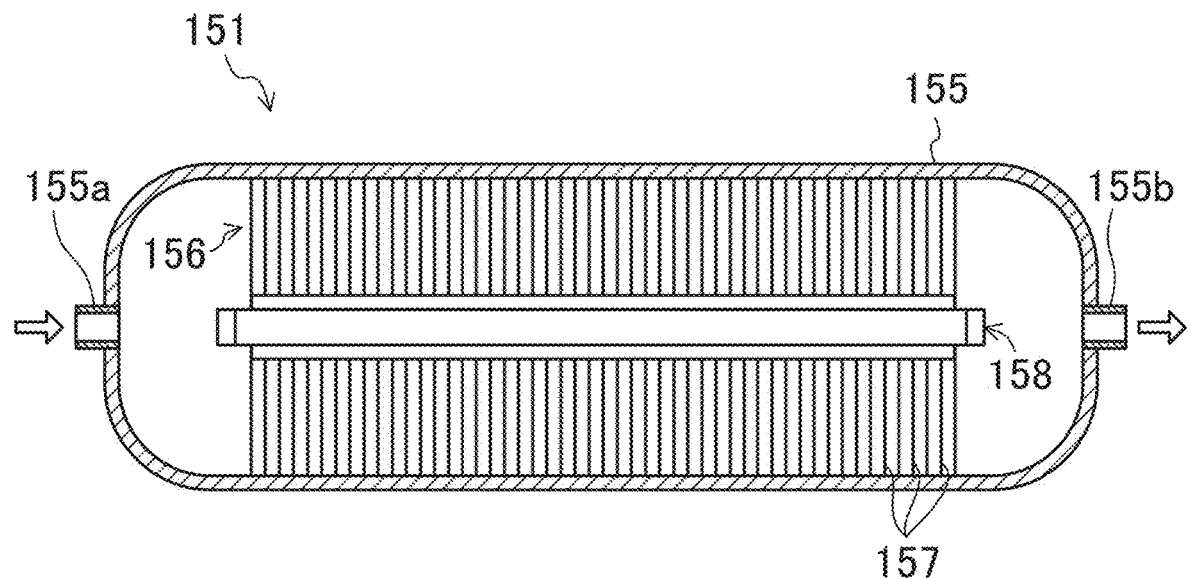
FIG. 4A is a schematic sectional view of a first air treatment unit provided in the internal air adjustment device of the embodiment.
Figure 4B:
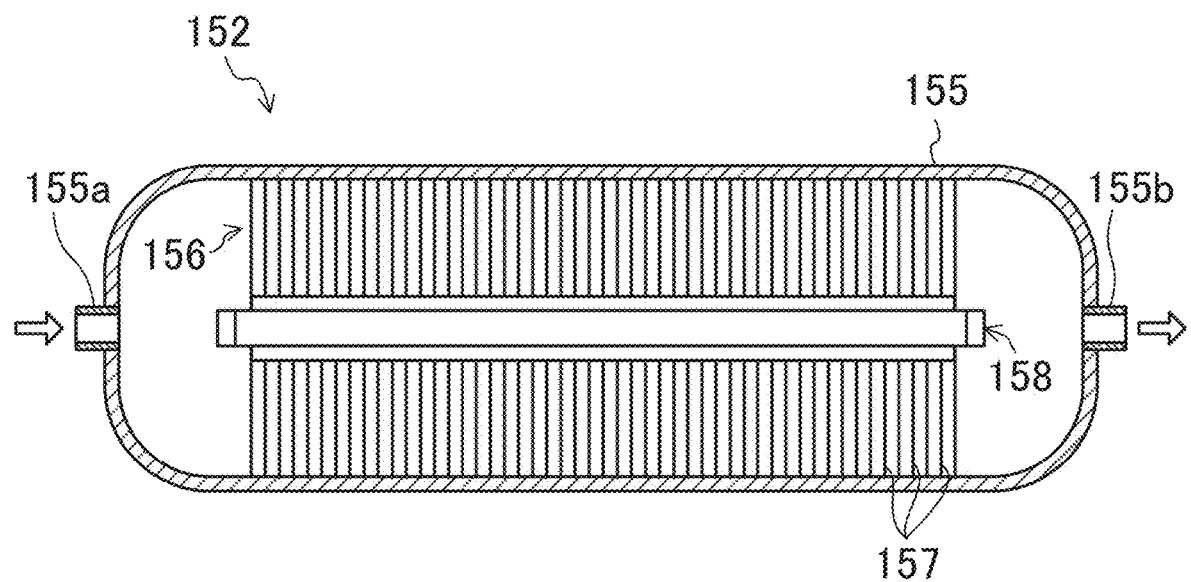
FIG. 4B is a schematic sectional view of a second air treatment unit provided in the internal air adjustment device of the embodiment.

As shown in FIGS. 4A and 4B, each of the first air treatment unit (151) and the second air treatment unit (152) includes a filter case (155), the photocatalyst filter (156), and an ultraviolet lamp (158).

The filter case (155) is an elongated cylindrical container having both ends closed. The filter case (155) has the air inlet (155*a*) in one end portion, and the air outlet (155*b*) in the other end portion. The air inlet (155*a*) and the air outlet (155*b*) are each a short tubular member and extend through a corresponding one of the end portions of the filter case (155).

The photocatalyst filter (156) is a cylindrical member constituted by stacking a plurality of filter elements (157) upon each other. The photocatalyst filter (156) is accommodated in the filter case (155) and is disposed at a central portion of the filter case (155) in an axial direction.

Figure 5:
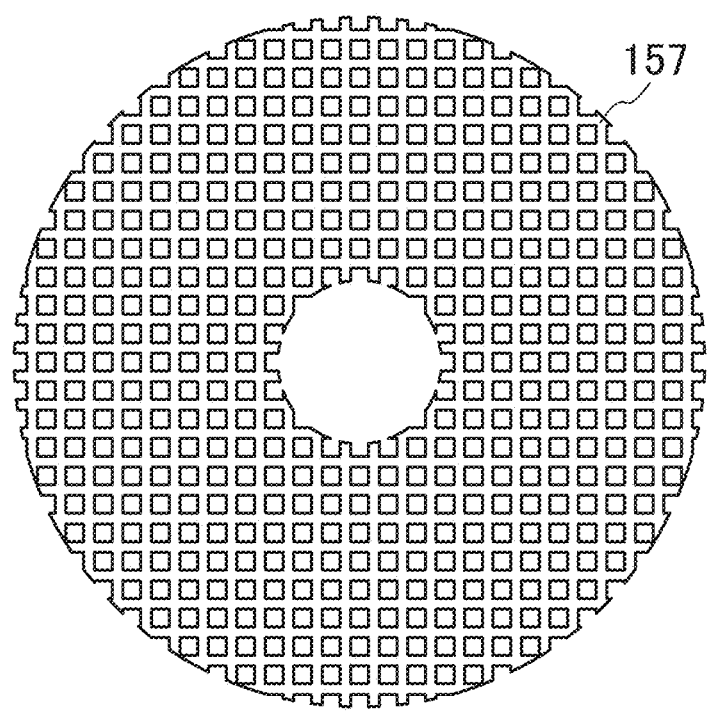
FIG. 5 is a schematic plan view of a filter element that constitutes a photocatalyst filter of the air treatment unit.

As shown in FIG. 5, each filter element (157) is a donut-shaped sheet member having a circular hole in a central portion thereof. In addition, each filter element (157) has many ventilation holes. A surface of each filter element (157) supports a material that functions as a photocatalyst (such as titanium dioxide/$TiO_2$).

As shown in FIGS. 4A and 4B, the ultraviolet lamp (158) has the shape of an elongated rod. The ultraviolet lamp includes a plurality of LEDs (light emitting diodes) that produce ultraviolet rays (electromagnetic waves having wavelengths of 100 nm to 400 nm). The ultraviolet lamp (158) is an ultraviolet light source, and radiates ultraviolet rays outward in a peripheral direction. The ultraviolet rays that are produced by the ultraviolet lamp (158) are desirably UV-C whose wavelength is primarily 280 nm or less.

As described above, the photocatalyst filter (156) is constituted by stacking the filter elements (157) having the shape shown in FIG. 5 upon each other. Therefore, a through hole extending in an axial direction of the cylindrical photocatalyst filter (156) is formed in the photocatalyst filter (156). The rod-shaped ultraviolet lamp (158) is inserted into the through hole of the photocatalyst filter (156). The ultraviolet lamp (158) is fixed to the filter case (155) through, for example, a stay outside the figure.

In each of the first and second air treatment units (151, 152), air that has flowed into the filter case (155) through the air outlet (155b) passes through the photocatalyst filter (156). In the photocatalyst filter (156), a photocatalyst of each filter element (157) is activated by the ultraviolet rays produced by the ultraviolet lamp (158). Microbes and ethylene in the air that passes through the photocatalyst filter (156) are oxidized and decomposed by the action of the photocatalyst. In the photocatalyst filter (156), by decomposing the microbes and the ethylene, $CO_2$ and $H_2O$ are produced.

<Separation Modules>

Figure 6A:
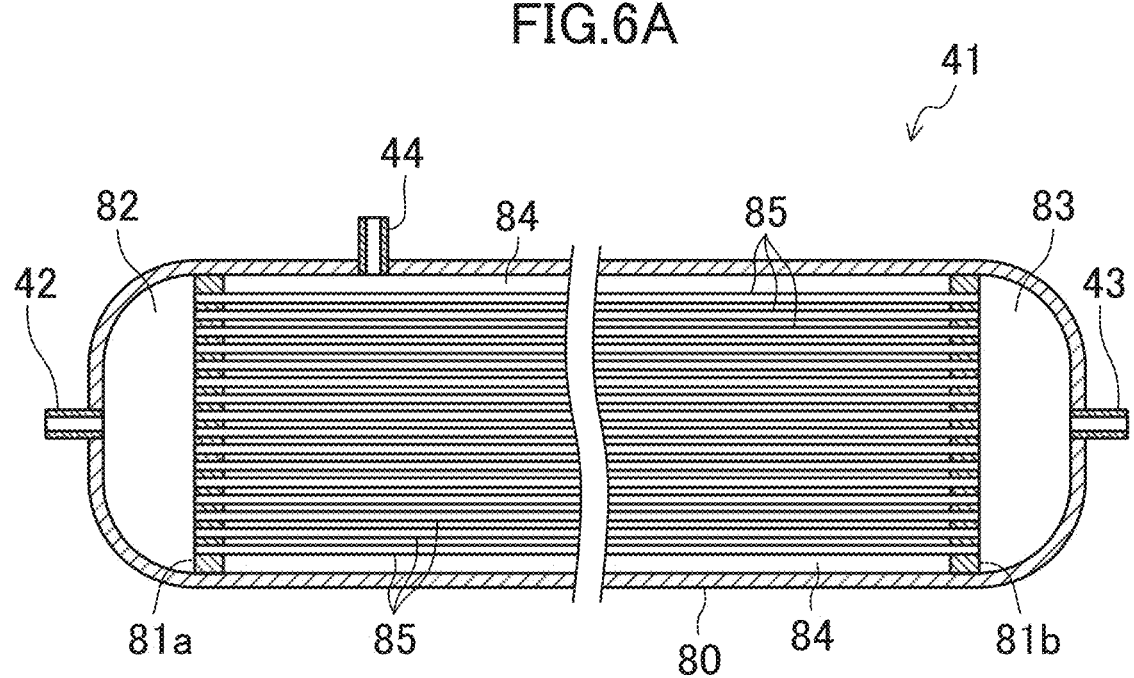
FIG. 6A is a schematic sectional view of a first separation module provided in the internal air adjustment device of the embodiment.
Figure 6B:
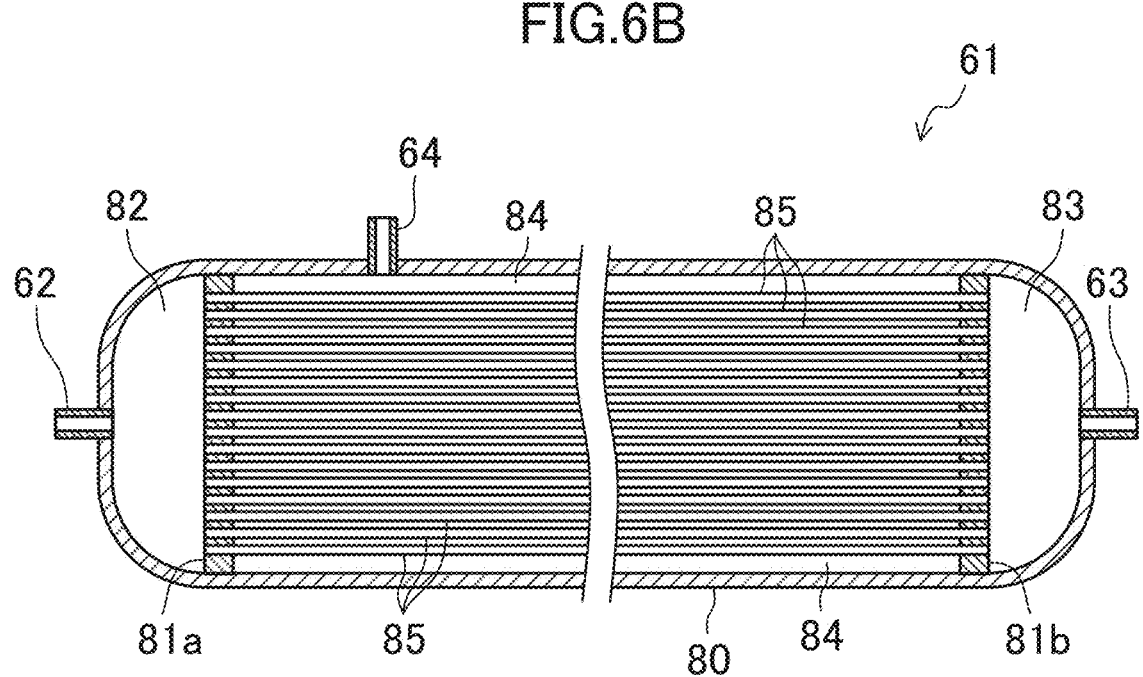
FIG. 6B is a schematic sectional view of a second separation module provided in the internal air adjustment device of the embodiment.

The structures of the first separation module (41) and the second separation module (61) are described with reference to FIGS. 6A and 6B. The structures of the first separation module (41) and the second separation module (61) are the same.

Each of the first separation module (41) and the second separation module (61) includes one cylindrical case (80) and two partition wall portions (81a, 81b). The cylindrical case (80) is an elongated cylindrical container having both ends closed. The partition wall portions (81a, 81b) are members for partitioning an internal space of the cylindrical case (80), and are disposed to cross the internal space of the cylindrical case (80). The partition wall portions (81a, 81b) are disposed, one at a position toward one end of the internal space of the cylindrical case (80) and the other at a position toward the other end of the internal space of the cylindrical case (80). In FIGS. 6A and 6B, the internal space of the cylindrical case (80) is partitioned into an introduction chamber (82) that is positioned to the left of the left partition wall portion (81a), a secondary exit chamber (84) that is positioned between the two partition wall portions (81a, 81b), and a primary exit chamber (83) that is positioned to the right of the right partition wall portion (81b).

Each of the first and second separation modules (41, 61) includes many gas separation membranes (85) that are formed into hollow thread-like portions (that is, very thin tubular portions whose outside diameter is 1 mm or less). The hollow thread-like gas separation membranes (85) are disposed from one partition wall portion (81a) to the other partition wall portion (81b). One end portion of each gas separation membrane (85) extends through the one partition wall portion (81a) and opens into the introduction chamber (82), and the other end portion of each gas separation membrane (85) extends through the other partition wall portion (81b) and opens into the primary exit chamber (83).

In the internal space of the cylindrical case (80), a portion of a space that is interposed between the two partition wall portions (81a, 81b) constitutes the secondary exit chamber (84), the portion being on an outer side of the gas separation membranes (85). In each of the first and second separation modules (41, 61), the introduction chamber (82) and the primary exit chamber (83) communicate with each other through the hollow thread-like gas separation membranes (85), whereas the secondary exit chamber (84) does not communicate with spaces on inner sides of the gas separation membranes (85), the introduction chamber (82), and the primary exit chamber (83).

The cylindrical case (80) for each of the first and second separation modules (41, 61) has the introduction port (42, 62), the primary exit port (43, 63), and the secondary exit port (44, 64), respectively. Each respective introduction port (42, 62) is disposed in a left end portion of the cylindrical case (80) in FIGS. 6A and 6B, and communicates with the introduction chamber (82). Each respective primary exit port (43, 63) is disposed in a right end portion of the cylindrical case (80) in FIGS. 6A and 6B, and communicates with the primary exit chamber (83). Each respective secondary exit port (44, 64) is disposed in an intermediate portion of the cylindrical case (80) in a longitudinal direction, and communicates with the secondary exit chamber (84).

Each gas separation membrane (85) is a non-porous membrane made of polymers. By making use of the fact that molecules pass through the gas separation membranes (85) at different speeds (passing speeds) according to material, the gas separation membranes (85) separate components in mixed gas.

In the internal air adjustment device (30) of the present embodiment, the first separation module (41) and the second separation module (61) each include the same gas separation membranes (85). The gas separation membranes (85) of each of the first and second separation modules (41, 61) have a characteristic that the passing speed of nitrogen is lower than both the passing speed of oxygen and the passing speed of carbon dioxide. The many hollow thread-like gas separation membranes (85) substantially have the same membrane thickness. Therefore, the gas separation membranes (85) of each of the first and second separation modules (41, 61) have the characteristic that the passing rate of nitrogen is lower than both the passing rate of oxygen and the passing rate of carbon dioxide.

In each of the first and second separation modules (41, 61), air that has flowed into the respective introduction chamber (82) through the respective introduction port (42, 62) flows in the spaces on the inner sides of respective the hollow thread-like gas separation membranes (85) toward the respective primary exit chamber (83). Part of the air that flows in the spaces on the inner sides of the gas separation membranes (85) passes through the gas separation membranes (85) and moves to the secondary exit chamber (84), and a remaining part thereof flows into the primary exit chamber (83).

The gas separation membranes (85) of each of the first and second separation modules (41, 61) are such that the passing rate of nitrogen is lower than the passing rate of oxygen and the passing rate of carbon dioxide. That is, nitrogen passes through the gas separation membranes (85) less easily than oxygen and carbon dioxide. Therefore, the air that flows on the inner sides of the hollow thread-like gas separation membranes (85) is such that, with decreasing distance to the primary exit chamber (83), the concentration of oxygen and the concentration of carbon dioxide thereof decrease at the same time that the concentration of nitrogen thereof increases. The oxygen and the carbon dioxide in air that flows in the hollow thread-like gas separation membranes (85) pass through the gas separation membranes (85) and move to the secondary exit chamber (84).

As a result, the air that has flowed into the primary exit chamber (83) without passing through the gas separation membranes (85) is such that the concentration of nitrogen thereof is higher than the concentration of nitrogen of the air in the introduction chamber (82) and the concentration of oxygen and the concentration of carbon dioxide thereof are lower than the concentration of oxygen and the concentration of carbon dioxide of the air in the introduction chamber (82). The air that has passed through the gas separation membranes (85) and that has moved to the secondary exit chamber (84) is such that the concentration of nitrogen thereof is lower than the concentration of nitrogen of the air in the introduction chamber (82) and the concentration of oxygen and the concentration of carbon dioxide thereof are higher than the concentration of oxygen and the concentration of carbon dioxide of the air in the introduction chamber (82).

In the first separation module (41), untreated external air flows into the introduction chamber (82) from the first introduction port (42), and the air that has flowed into the primary exit chamber (83) without passing through the gas separation membranes (85) flows out the first primary exit port (43) as first external air, and the air that has passed through the gas separation membranes (85) and flowed into the secondary exit chamber (84) flows out the first secondary exit port (44) as second external air. On the other hand, in the second separation module (61), untreated internal air flows into the introduction chamber (82) from the second introduction port (62), and the air that has flowed into the primary exit chamber (83) without passing through the gas separation membranes (85) flows out the secondary primary exit port (63) as first internal air, and the air that has passed through the gas separation membranes (85) and flowed into the secondary exit chamber (84) flows out the second secondary exit port (64) as second internal air.

<Sensor Unit>

As shown in FIGS. 1 and 3, the sensor unit (90) is disposed at the secondary flow path (29b) of the internal air flow path (29) of the container refrigerating machine (10). As shown in FIG. 3, the sensor unit (90) includes an oxygen sensor (91), a carbon dioxide sensor (92), and a sensor case (93).

The oxygen sensor (91) is a zirconia current sensor that measures the concentration of oxygen of mixed gas, such as air. The carbon dioxide sensor (92) is a non dispersive infrared (NDIR) sensor that measures the concentration of carbon dioxide of mixed gas, such as air. The oxygen sensor (91) and the carbon dioxide sensor (92) are accommodated in the sensor case (93).

The sensor case (93) is a slightly elongated box-shaped member. An outlet end of the measurement pipe (125) is connected to one end portion in a longitudinal direction of the sensor case (93), and one end of an outlet pipe (95) is connected to the other end portion in the longitudinal direction of the sensor case (93). The other end of the outlet pipe (95) opens into the primary flow path (29a) of the internal air flow path (29). An air filter (94) for introducing internal air that flows in the internal air flow path (29) into an internal space of the sensor case (93) is mounted on the sensor case (93). The air filter (94) is a membrane filter for trapping, for example, dust in the internal air.

As described above, when the internal fan (17) is operating, the air pressure of the secondary flow path (29b) is slightly higher than the air pressure of the primary flow path (29a). Therefore, when the measurement on-off valve (126) is in a closed state, internal air in the secondary flow path (29b) flows into the sensor case (93) through the air filter (94), and then flows into the primary flow path (29a) through the outlet pipe (95). In this state, in the sensor unit (90), the oxygen sensor (91) measures the concentration of oxygen of the internal air, and the carbon dioxide sensor (92) measures the concentration of carbon dioxide of the internal air.

<Ventilation Discharge Pipe>

The ventilation discharge pipe (100) is a pipe for connecting the inside and the outside of the transport container (1). The ventilation discharge pipe (100) constitutes a ventilation discharge passage. As shown in FIG. 1, the ventilation discharge pipe (100) extends through the casing (20) of the container refrigerating machine (10). One end of the ventilation discharge pipe (100) opens into the secondary flow path (29b) of the internal air flow path (29). The other end of the ventilation discharge pipe (100) opens on the suction side of the external fan (16) in the external machine room (28).

As shown in FIG. 3, an air filter (102) is mounted on the one end of the ventilation discharge pipe (100). The air filter (102) is a membrane filter for trapping, for example, dust in the internal air. In addition, a ventilation discharge valve (101) is provided at the ventilation discharge pipe (100). The ventilation discharge valve (101) is an on-off valve constituted by an electromagnetic valve.

<Control Unit>

The control unit (110) includes a CPU (111) that performs a control operation and a memory (112) that stores, for example, data required for the control operation. Measurement values of the oxygen sensor (91), the carbon dioxide sensor (92), the first pressure sensor (45), and the second pressure sensor (65) are input to the control unit (110). The control unit (110) performs the control operation for operating the first pump (35), the second pump (37), the first control valve (46), the second control valve (66), and the ventilation discharge valve (101).

—Operations of Container Refrigerating Machine—

The container refrigerating machine (10) performs a cooling operation of cooling internal air of the transport container (1).

In the cooling operation, a vapor compression refrigeration cycle is performed by operating the compressor (12) of the refrigerant circuit (11) and circulating a refrigerant in the refrigerant circuit (11). In the refrigerant circuit (11), the refrigerant discharged from the compressor (12) passes through the condenser (13), the expansion valve (14), and the evaporator (15) in this order, and then is sucked into and compressed by the compressor (12).

In the cooling operation, the external fan (16) and the internal fan (17) operate. When the external fan (16) operates, external air existing outside the transport container (1) is sucked into the external machine room (28) and passes through the condenser (13). At the condenser (13), the refrigerant dissipates heat to the external air and is condensed. When the internal fan (17) operates, internal air in the load room (5) of the transport container (1) is sucked into the internal air flow path (29) and passes through the evaporator (15). At the evaporator (15), the refrigerant absorbs heat from the internal air and evaporates.

Flow of internal air is described. Internal air existing in the load room (5) flows through the suction port (26) and flows into the primary flow path (29a) of the internal air flow path (29), and is blown out to the secondary flow path (29b) by the internal fan (17). The internal air that has flowed into the secondary flow path (29b) is, when passing through the evaporator (15), cooled, and then is blown out to the underfloor flow path (4) from the blow-out port (27), passes through the underfloor flow path (4), and flows into the load room (5).

In the internal air flow path (29), the primary flow path (29a) is positioned on a suction side of the internal fan (17) and the secondary flow path (29b) is positioned on a blow-out side of the internal fan (17). Therefore, when the internal fan (17) is operating, the air pressure of the secondary flow path (29b) is slightly higher than the air pressure of the primary flow path (29a).

—Operations of Internal Air Adjustment Device—

The internal air adjustment device (30) performs an operation for adjusting the composition of internal air (in the present embodiment, the concentration of oxygen and the concentration of carbon dioxide of the internal air) in the load room (5) of the transport container (1). In the operation, the internal air adjustment device (30) performs a first oxygen concentration reduction operation, a second oxygen concentration reduction operation, an oxygen concentration increasing operation, and a carbon dioxide concentration reduction operation while switching between them as appropriate.

During the operation of the internal air adjustment device (30), the control unit (110) obtains measurement values of the oxygen sensor (91) and the carbon dioxide sensor (92). The control unit (110) controls the structural components of the internal air adjustment device (30) based on the measurement values of the oxygen sensor (91) and the carbon dioxide sensor (92) to maintain the concentration of oxygen and the concentration of carbon dioxide of the internal air to within respective target ranges.

<First Oxygen Concentration Reduction Operation>

The first oxygen concentration reduction operation is an operation for reducing the concentration of oxygen in the internal air existing in the load room (5). In the first oxygen concentration reduction operation of the internal air adjustment device (30), the first composition adjuster (40) supplies first external air having a low concentration of oxygen to the load room (5) and the second composition adjuster (60) supplies first internal air having a low concentration of oxygen to the load room (5).

In the first oxygen concentration reduction operation, the control unit (110) sets the first primary switching valve (56) and the first secondary switching valve (58) to the respective first states (the states shown by the solid lines in FIG. 3), and sets the second primary switching valve (76) and the second secondary switching valve (78) to the respective first states (the states shown by the broken lines in FIG. 3). The control unit (110) operates the first pump (35) and the second pump (37) and sets the ventilation discharge valve (101) in an open state.

When the first pump (35) operates, external air existing outside the transport container (1) passes through the air filter (47) and the external-side suction pipe (55), and flows into the first air treatment unit (151). In the first air treatment unit (151), the photocatalyst of the photocatalyst filter (156) is subjected to ultraviolet rays produced by the ultraviolet lamp (158), and is activated. The external air that has flowed into the first air treatment unit (151) passes through the photocatalyst filter (156), and, in the process thereof, decomposes microbes in external air.

The external air that has flowed out the first air treatment unit (151) is sucked into the first pump (35). The first pump (35) compresses and discharges the external air that has been sucked in. The external air discharged from the first pump (35) flows in the first introduction pipe (52) and flows into the first introduction port (42) of the first separation module (41) as untreated external air.

The untreated external air that has flowed into the first separation module (41) is separated into first external air that did not pass through the gas separation membranes (85) and second external air that has passed through the gas separation membranes (85). The concentration of oxygen of the first external air is lower than the concentration of oxygen of the untreated external air, and the concentration of oxygen of the second external air is higher than the concentration of oxygen of the untreated external air. The first external air flows out the first primary exit port (43), passes through the first primary pipe (53), and flows into the supply pipe (120). The second external air flows out the first secondary exit port (44), passes through the first secondary pipe (54), and is discharged to the outside of the transport container (1).

When the second pump (37) operates, internal air existing in the transport container (1) (specifically, the secondary flow path (29b) of the container refrigerating machine (10)) passes through the internal-side suction pipe (75), and flows into the second air treatment unit (152). In the second air treatment unit (152), the photocatalyst of the photocatalyst filter (156) is subjected to ultraviolet rays produced by the ultraviolet lamp (158), and is activated. Internal air that has flowed into the second air treatment unit (152) passes through the photocatalyst filter (156), and, in the process thereof, decomposes ethylene and microbes in the internal air.

The internal air that has flowed out the second air treatment unit (152) is sucked into the second pump (37). The second pump (37) compresses and discharges the internal air that has been sucked in. The internal air discharged from the second pump (37) flows in the second introduction pipe (72) and flows into the second introduction port (62) of the second separation module (61) as untreated internal air.

The untreated internal air that has flowed into the second separation module (61) is separated into first internal air that did not pass through the gas separation membranes (85) and second internal air that has passed through the gas separation membranes (85). The concentration of oxygen of the first internal air is lower than the concentration of oxygen of the untreated internal air, and the concentration of oxygen of the second internal air is higher than the concentration of oxygen of the untreated internal air. The first internal air flows out the second primary exit port (63), passes through the second primary pipe (73), and flows into the supply pipe (120). The second internal air flows out the second secondary exit port (64), passes through the second secondary pipe (74), and is discharged to the outside of the transport container (1).

As described above, the first external air that has flowed out the first separation module (41) and the first internal air that has flowed out the second separation module (61) flow into the supply pipe (120). Mixed air containing the first external air and the first internal air that flow in the supply pipe (120) flows into the secondary flow path (29b) of the container refrigerating machine (10) and is supplied, together with air that flows in the secondary flow path (29b), to the load room (5).

<Second Oxygen Concentration Reduction Operation>

The second oxygen concentration reduction operation is an operation for reducing the concentration of oxygen of the internal air existing in the load room (5) while suppressing a reduction in the concentration of carbon dioxide thereof. In the second oxygen concentration reduction operation of the internal air adjustment device (30), the first composition adjuster (40) supplies first external air having a low concentration of oxygen to the load room (5) and the second composition adjuster (60) supplies second internal air having a high concentration of carbon dioxide to the load room (5).

In the second oxygen concentration reduction operation, the control unit (110) sets the first primary switching valve (56) and the first secondary switching valve (58) to the respective first states (the states shown by the solid lines in FIG. 3), and sets the second primary switching valve (76) and the second secondary switching valve (78) to the respective second states (the states shown by the solid lines in FIG. 3). The control unit (110) operates the first pump (35) and the second pump (37) and sets the ventilation discharge valve (101) in an open state.

The operation that is performed by the first composition adjuster (40) during the second oxygen concentration reduction operation is the same as the operation that is performed during the first oxygen concentration reduction operation. That is, in the first composition adjuster (40), the internal air treated at the first air treatment unit (151) is separated into first external air and second external air at the first separation module (41). Then, in the first composition adjuster (40), the first external air whose concentration of oxygen is lower than the concentration of oxygen of untreated external air passes through the first primary pipe (53) and is supplied to the supply pipe (120), and the second external air whose concentration of oxygen is higher than the concentration of oxygen of untreated external air passes through the first secondary pipe (54) and is discharged to the outside of the transport container (1).

In the second composition adjuster (60), as during the first oxygen concentration reduction operation, the internal air passes through the second air treatment unit (152) and the second pump (37) in this order, and then flows into the second separation module (61). In the second air treatment unit (152), ethylene and microbes in the internal air are decomposed by the photocatalyst filter (156), as a result of which $CO_2$ and $H_2O$ are produced. Therefore, the internal air (untreated internal air) that flows into the second separation module (61) contains carbon dioxide produced by the breathing of plants (6) stored in the load room (5) and the carbon dioxide produced by the second air treatment unit (152).

The untreated internal air that has flowed into the second separation module (61) is separated into first internal air that did not pass through the gas separation membranes (85) and second internal air that has passed through the gas separation membranes (85). The concentration of carbon dioxide of the first internal air is lower than the concentration of carbon dioxide of the untreated internal air, and the concentration of carbon dioxide of the second internal air is higher than the concentration of carbon dioxide of the untreated internal air. The first internal air flows out the second primary exit port (63), passes through the second primary pipe (73), the second primary switching valve (76), and the second primary discharge pipe (77) in this order, and is discharged to the outside of the transport container (1). The second external air flows out the second secondary exit port (64), passes through the second secondary pipe (74), the second secondary switching valve (78), and the second secondary supply pipe (79) in this order, and flows into the supply pipe (120).

As described above, the first external air that has flowed out the first separation module (41) and the second internal air that has flowed out the second separation module (61) flow into the supply pipe (120). Mixed air containing the first external air and the second internal air that flow in the supply pipe (120) flows into the secondary flow path (29b) of the container refrigerating machine (10) and is supplied, together with air that flows in the secondary flow path (29b), to the load room (5).

<Oxygen Concentration Increasing Operation>

The oxygen concentration increasing operation is an operation for increasing the concentration of oxygen of internal air existing in the load room (5). In the oxygen concentration increasing operation, the first composition adjuster (40) supplies to the load room (5) external air as it is that has been sucked in from the outside of the transport container (1), and the second composition adjuster (60) sends back to the load room (5) internal air as it is that has been sucked in from the inside of the transport container (1).

In the oxygen concentration increasing operation, the control unit (110) sets the first primary switching valve (56) and the second primary switching valve (76) to the respective first states, and sets the first secondary switching valve (58) and the second secondary switching valve (78) to the respective second states. The control unit (110) operates the first pump (35) and the second pump (37), sets the ventilation discharge valve (101) in an open state, and sets the measurement on-off valve (126) in a closed state.

In the first composition adjuster (40), the external air passes through the first air treatment unit (151) and the first pump (35) in this order, and then flows into the first separation module (41). In the first air treatment unit (151), microbes in the external air are decomposed by the photocatalyst filter (156). The external air that has flowed into the first separation module (41) is temporarily separated into first external air and second external air. The first external air passes through the first primary pipe (53) and is supplied to the supply pipe (120). The second external air passes through the first secondary pipe (54) and the first secondary supply pipe (59) in this order and is supplied to the supply pipe (120). The first composition adjuster (40) supplies both the first external air and the second external air to the load room (5) through the supply pipe (120).

In the second composition adjuster (60), the internal air passes through the second air treatment unit (152) and the second pump (37) in this order, and flows into the second separation module (61). In the second air treatment unit (152), microbes and ethylene in the internal air are decomposed by the photocatalyst filter (156). The internal air that has flowed into the second separation module (61) is temporarily separated into first internal air and second internal air. The first internal air passes through the second primary pipe (73) and is supplied to the supply pipe (120). The second internal air passes through the second secondary pipe (74) and the second secondary supply pipe (79) in this order and is supplied to the supply pipe (120). The second composition adjuster (60) supplies both the first internal air and the second internal air to the load room (5) through the supply pipe (120).

<Carbon Dioxide Concentration Reduction Operation>

The carbon dioxide concentration reduction operation is an operation for reducing the concentration of carbon dioxide in internal air existing in the load room (5). In the carbon dioxide concentration reduction operation, the first composition adjuster (40) and the second composition adjuster (60) perform the same operation as that performed during the first oxygen reduction operation.

The concentration of carbon dioxide of the atmosphere is 0.04%. Therefore, the concentration of carbon dioxide of first external air separated from untreated external air is, similarly to the concentration of carbon dioxide of the atmosphere, very low. Consequently, the first composition adjuster (40) supplies the first external air having a low concentration of carbon dioxide to the load room (5).

In the second separation module (61) of the second composition adjuster (60), untreated internal air is separated into first internal air and second internal air. The concentration of carbon dioxide of the first internal air is lower than the concentration of carbon dioxide of the untreated internal air. The concentration of carbon dioxide of the second internal air is higher than the concentration of carbon dioxide of the untreated internal air. Therefore, the second composition adjuster (60) supplies the first internal air having a low concentration of carbon dioxide to the load room (5), and discharges the second internal air having a high concentration of carbon dioxide to the outside of the transport container (1).

—Characteristic (1) of Embodiment—

The internal air adjustment device (30) of the present embodiment adjusts the composition of internal air in the transport container (1). The internal air adjustment device (30) includes the internal-side passage (70) and the first air treatment unit (151). The internal-side passage (70) has the second separation module (61). The second separation module (61) separates from internal air in the transport container (1) return air having a composition that differs from the composition of the internal air. The internal-side passage (70) sends the internal air to the second separation module (61) from the inside of the transport container (1) and sends the return air into the transport container (1) from the second separation module (61). The first air treatment unit (151) decomposes ethylene in air that flows in the internal-side passage (70).

In the internal air adjustment device (30) of the present embodiment, the internal air flows in the internal-side passage (70) and flows into the second separation module (61). The second separation module (61) separates the return air from the internal air. The return air passes through the internal-side passage (70) and is supplied into the transport container (1). The composition of the return air differs from the composition of the internal air. Therefore, by supplying the return air into the transport container (1), the composition of the internal air existing in the transport container (1) is controlled.

In the present embodiment, the first air treatment unit (151) is provided in the internal air adjustment device (30). The first air treatment unit (151) decomposes ethylene in air that flows in the internal-side passage (70). When ethylene is contained in the internal air that flows into the internal-side passage (70), a part or all of the ethylene is removed at the first air treatment unit (151). The amount of ethylene in the return air that is supplied into the transport container (1) from the internal-side passage (70) becomes smaller than the amount of ethylene in the internal air that flows into the internal-side passage (70). Therefore, by supplying the return air into the transport container (1), the concentration of ethylene of the internal air existing in the transport container (1) is controlled.

In this way, the internal air adjustment device (30) of the present embodiment is capable of controlling both the composition of internal air and the concentration of ethylene. Therefore, it can be made more convenient for, for example, a company that controls the quality of the storage products (6) in the transport container (1).

In addition, in the present embodiment, the first air treatment unit (151) that decomposes microbes in external air and the second air treatment unit (152) that decomposes microbes and ethylene in internal air are installed in the internal air adjustment device (30) for adjusting the composition of the internal air. Therefore, according to the present embodiment, it is possible to, while preventing an increase in the size of a device that controls an internal environment of the transport container (1), suppress a reduction in the quality of the storage products (6) by properly controlling the internal environment of the transport container (1).

—Characteristic (2) of Embodiment—

In the internal air adjustment device (30) of the present embodiment, the first air treatment unit (151) further decomposes microbes in internal air.

In the internal air adjustment device (30) of the present embodiment, the first air treatment unit (151) decomposes ethylene in air that flows in the internal-side passage (70) and decomposes microbes in the air that flows in the internal-side passage (70). The internal air of the transport container (1) may include microbes, such as mold spores or floating bacteria. When such microbes adhere to the storage products (6) and develop, the quality of the storage products (6) is reduced. On the other hand, the first air treatment unit (151) of the present embodiment decomposes microbes in the air that flows in the internal-side passage (70). As a result, the number of microbes existing in the transport container (1) is reduced, and the number of storage products (6) to be thrown away due to a reduction in quality, such as spoilage, can be reduced.

—Characteristic (3) of Embodiment—

In the internal air adjustment device (30) of the present embodiment, the first air treatment unit (151) includes the ultraviolet lamp (158) and the photocatalyst filter (156). The ultraviolet lamp (158) produces ultraviolet rays. The photocatalyst filter (156) is subjected to the ultraviolet rays produced by the ultraviolet lamp (158), and decomposes ethylene and microbes.

In the first air treatment unit (151) of the present embodiment, the ultraviolet lamp (158) produces ultraviolet rays, and the photocatalyst filter (156) that has been activated by the ultraviolet rays decomposes ethylene and microbes in air that flows in the internal-side passage (70).

—Characteristic (4) of Embodiment—

In the internal air adjustment device (30) of the present embodiment, the second separation module (61) in the internal-side passage (70) separates from internal air return air whose concentration of carbon dioxide is higher than the concentration of carbon dioxide of the internal air. The first air treatment unit (151) is disposed upstream from the second separation module (61) in the internal-side passage (70).

In the internal air adjustment device (30) of the present embodiment, the first air treatment unit (151) decomposes ethylene and microbes. When the ethylene and the microbes are decomposed (oxidized), carbon dioxide is produced. The carbon dioxide produced in the first air treatment unit (151) flows, together with the internal air that has flowed into the internal-side passage (70) from the transport container (1), into the second separation module (61). The second separation module (61) separates the return air from the internal air. The return air contains, in addition to carbon dioxide in the internal air that flows in the internal-side passage (70), the carbon dioxide produced in the internal-side treatment unit (152).

The return air having a concentration of carbon dioxide that is higher than the concentration of carbon dioxide of the internal air that has flowed into the internal-side passage (70) is supplied into the transport container (1). Therefore, according to the embodiment, the carbon dioxide produced by decomposing ethylene and microbes can be used for adjusting the concentration of carbon dioxide of the internal air in the transport container (1).

—Characteristic (5) of Embodiment—

The internal air adjustment device (30) of the present embodiment includes the external-side passage (50) and the second air treatment unit (152). The external-side passage (50) has the first separation module (41). The first separation module (41) separates from external air outside the transport container (1) supply air having a composition that differs from the composition of the external air. The external-side passage (50) sends the external air to the first separation module (41) from the outside of the transport container (1), and sends the supply air into the transport container (1) from the first separation module (41). The second air treatment unit (152) is provided at the external-side passage (50) and decomposes microbes in the external air.

In the internal air adjustment device (30) of the present embodiment, the external air flows in the external-side passage (50) and flows into the first separation module (41). The first separation module (41) separates the return air from the external air. The return air passes through the external-side passage (50) and is supplied into the transport container (1). The composition of the return air differs from the composition of the external air. Therefore, by supplying the return air into the transport container (1), the composition of the internal air existing in the transport container (1) is controlled.

In the present embodiment, the second air treatment unit (152) is provided in the internal air adjustment device (30). The second air treatment unit (152) decomposes microbes in air that flows in the external-side passage (50). The external air may contain microbes, such as mold spores or floating bacteria. When such microbes adhere to the storage products (6) and develop, the quality of the storage products (6) is reduced. On the other hand, the second air treatment unit (152) of the present embodiment decomposes microbes in the air that flows in the external-side passage (50). As a result, the number of microbes existing in the transport container (1) is reduced, and the number of storage products (6) to be thrown away due to a reduction in quality, such as spoilage, can be reduced.

—Characteristic (6) of Embodiment—

In the internal air adjustment device (30) of the present embodiment, the second air treatment unit (152) includes the ultraviolet lamp (158) and the photocatalyst filter (156). The ultraviolet lamp (158) produces ultraviolet rays. The photocatalyst filter (156) is subjected to the ultraviolet rays produced by the ultraviolet lamp (158), and decomposes ethylene and microbes.

In the second air treatment unit (152) of the present embodiment, the ultraviolet lamp (158) produces ultraviolet rays, and the photocatalyst filter (156) that has been activated by the ultraviolet rays decomposes microbes in the air that flows in the external-side passage (50).

—Modifications of Embodiments—

Regarding the internal air adjustment device (30) of each embodiment above, the following modifications may be applied. Note that the modifications below may be combined or replaced as appropriate as long as the functions of the internal air adjustment device (30) are not impaired.

<Modification 1>

In the first composition adjuster (40) of the present embodiment, the first air treatment unit (151) may be disposed between the first pump (35) and the first separation module (41) in the external-side passage (50). In the second composition adjuster (60) of the present embodiment, the second air treatment unit (152) may be disposed between the second pump (37) and the second separation module (61) in the internal-side passage (70).

<Modification 2>

The second air treatment unit (152) of the present embodiment may include, in place of the photocatalyst filter (156) or in addition to the photocatalyst filter (156), an adsorbent that adsorbs ethylene. The second air treatment unit (152) of the present modification traps ethylene in internal air.

<Modification 3>

In the internal air adjustment device (30) of the present embodiment, the first pump (35) and the second pump (37) may be driven by one motor.

<Modification 4>

The first composition adjuster (40) and the second composition adjuster (60) of the present embodiment may each be constituted to separate sucked air into two types of air having compositions differing from each other by a so-called PSA (Pressure Swing Adsorption) method. In this case, the composition adjusters (40, 60) repeat a step of producing air having a low concentration of nitrogen and a high concentration of oxygen and a high concentration of carbon dioxide by adsorbing nitrogen in the sucked air onto an adsorbent and a step of producing air having a high concentration of nitrogen and a low concentration of oxygen and a low concentration of carbon dioxide by desorbing the nitrogen from the adsorbent.

<Modification 5>

The internal air adjustment device (30) of the present embodiment may be provided in a stationary refrigerator or freezer. The internal air adjustment device (30) of each embodiment above may be provided in a refrigerating/freezing container for land transportation, transported by, for example, truck or rail. The internal air adjustment device (30) of each embodiment above may be provided in a refrigerating/freezing truck in which a box body that forms a load room is integrated with a chassis.

Although the embodiments and modifications have been described above, it will be understood that various changes in form and detail can be made without departing from the spirit and scope of the claims. The embodiments and the modifications above may be combined or replaced as appropriate as long as the object functions of the present disclosure are not impaired.

INDUSTRIAL APPLICABILITY

As described above, the present disclosure is useful for an internal air adjustment device.

REFERENCE SIGNS LIST 1 transport container (storage)
30 internal air adjustment device
41 first separation module (external-side separator)
50 external-side passage
61 second separation module (internal-side separator)
70 internal-side passage
151 first air treatment unit (internal-side treatment unit)
152 second air treatment unit (external-side treatment unit)
156 photocatalyst filter (photocatalyst)
158 ultraviolet lamp (ultraviolet light source)

The invention claimed is:

1. An internal air adjustment device that adjusts a composition of internal air in an inside of a storage, comprising:
an internal-side passage including an internal-side separator, the internal-side passage sending the internal air to the internal-side separator from the inside of the storage and sending return air to the inside of the storage from the internal-side separator; and an internal-side treatment unit configured to perform decomposition of ethylene in air that flows in the internal-side passage, wherein the internal-side separator is configured to separate untreated internal air, which is the internal air having flowed into the internal-side separator from the inside of the storage, into first internal air and second internal air, and to cause one of the first internal air or the second internal air to flow out as the return air, a concentration of nitrogen of the first internal air is higher than that of the untreated internal air, and a concentration of oxygen and a concentration of carbon dioxide of the first internal air are respectively lower than those of the untreated internal air, a concentration of nitrogen of the second internal air is lower than that of the untreated internal air, and a concentration of oxygen and a concentration of carbon dioxide of the second internal air are respectively higher than those of the untreated internal air, and the internal-side treatment unit includes:
  an ultraviolet light source configured to produce ultraviolet rays;
  a photocatalyst subjected to the ultraviolet rays produced by the ultraviolet light source and decomposes ethylene and microbes; and
  a case that accommodates the ultraviolet light source and the photocatalyst.

2. The internal air adjustment device according to claim 1,
  wherein the internal-side separator in the internal-side passage is configured to cause the second internal air to flow out as the return air, and
  wherein the internal-side treatment unit is disposed upstream from the internal-side separator in the internal-side passage.

3. The internal air adjustment device according to claim 1, comprising:
  an external-side passage including an external-side separator, the external-side passage sending external air to the external-side separator from an outside of the storage and sending supply air to the inside of the storage from the external-side separator; and
  an external-side treatment unit provided at the external-side passage and configured to decompose microbes in the external air, wherein
  the external-side separator is configured to separate untreated external air, which is the external air having flowed into the external-side separator from the outside of the storage, into first external air and second external air, and to cause one of the first external air or the second external air to flow out as the supply air,
  a concentration of nitrogen of the first external air is higher than that of the untreated external air, and a concentration of oxygen and a concentration of carbon dioxide of the first external air are respectively lower than those of the untreated external air, and
  a concentration of nitrogen of the second external air is lower than that of the untreated external air, and a concentration of oxygen and a concentration of carbon dioxide of the second external air are respectively higher than those of the untreated external air.

* * * * *